(12) United States Patent
Heilenkötter

(10) Patent No.: US 6,715,344 B2
(45) Date of Patent: Apr. 6, 2004

(54) PROCESS FOR DETERMINING THE CURRENT STATE OF A LUBRICANT

(75) Inventor: Dirk Heilenkötter, Dannenbüttel (DE)

(73) Assignee: Volkswagen AG, Wolfsburg (DE)

( * ) Notice: Subject to any disclaimer, the term of this patent is extended or adjusted under 35 U.S.C. 154(b) by 219 days.

(21) Appl. No.: 09/853,016

(22) Filed: May 10, 2001

(65) Prior Publication Data
US 2001/0054304 A1 Dec. 27, 2001

(30) Foreign Application Priority Data
Jun. 23, 2000 (DE) .......................... 100 30 854

(51) Int. Cl.[7] .............................. G01N 33/26
(52) U.S. Cl. ........................................ 73/53.05
(58) Field of Search ............ 73/10, 53.05, 53.06, 73/54.39, 118; 340/438

(56) References Cited

U.S. PATENT DOCUMENTS

| 3,823,599 A | * | 7/1974 | Litz et al. | |
|---|---|---|---|---|
| 3,913,377 A | * | 10/1975 | Lindeman | |
| 4,311,036 A | * | 1/1982 | Kajdas et al. | 73/10 |
| 5,932,790 A | | 8/1999 | Hoffman et al. | 73/10 |
| 6,018,198 A | * | 1/2000 | Tsuzuki et al. | 290/17 |
| 6,112,573 A | * | 9/2000 | Thelen | 73/10 |
| 6,139,471 A | * | 10/2000 | Tsutsui et al. | 477/156 |

FOREIGN PATENT DOCUMENTS

| DE | 3933973 | 4/1991 |
|---|---|---|
| DE | 19644029 | 5/1998 |
| EP | 0219913 | 4/1987 |
| EP | 0297643 | 1/1989 |
| WO | 9839631 | 9/1998 |
| WO | 9945381 | 9/1999 |

OTHER PUBLICATIONS

English-language abstract for DE 196 44 029.
English-language abstract for DE 39 33 973.

* cited by examiner

*Primary Examiner*—Robert Raevis
(74) *Attorney, Agent, or Firm*—Baker Botts L.L.P.

(57) ABSTRACT

A method for determining the current state of a lubricant for lubrication of at least two frictional coupling elements capable of cooperating to transmit a torque by comparing reference slip characteristics associated with particular operating conditions with current slip characteristics of the coupling elements is disclosed.

13 Claims, 1 Drawing Sheet

PROCESS FOR DETERMINING THE CURRENT STATE OF A LUBRICANT

BACKGROUND OF THE INVENTION

This invention relates to a process for determining the current state of a lubricant that lubricates at least one pair of frictional coupling elements which cooperate at least some of the time to transmit a torque, and, in particular, for determining the current state of the transmission oil for lubrication of two wet-running frictional coupling elements of a transmission, wherein the cooperating coupling elements have certain slip characteristics at a specific quality state of the lubricant.

In wet-running clutches comprised of two frictional coupling elements selectively engagable to transmit a torque, "microslip" is present between the coupling elements even when engaged in the lower portion of the specified load range. This microslip increases as the load increases, i.e. as the torque to be transmitted increases, rising slowly but steadily into the region of "macroslip". When the frictional coupling element lubricant degrades due to the factors discussed below, the slip characteristics of the frictional coupling elements change and microslip no longer occurs at low torque, leading to an abrupt transition to macroslip when a certain torque threshold is exceeded.

Lubricants are subject to degradation caused by temperature fluctuations, length of time the lubricant is used, type and manner of use and contamination of the lubricant. Degraded lubricants are ineffective at protecting the elements they lubricate from damage caused by friction. Additionally, degraded lubricant can lead to damage to components connected to the elements the lubricant protects. For example, components within a transmission, such as gears, synchronizers and sliding sleeves can be damaged when the frictional coupling elements in the clutch connected to the transmission are lubricated by degraded lubricant. Consequently, lubricants must be replaced after an appropriate period of use. With regard to engine lubricants in motor vehicles, it is customary to replace such lubricant after every 15,000 km or 30,000 km driven or after a particular amount of time, e.g. every 12 months. To alert the driver of a motor vehicle that it is time for an oil change, it is known to provide appropriate visual displays in the passenger compartment which are activated in response to signals (typically generated by an on-board computer) based on the mileage driven. However, such methods do not account for premature degradation in the lubricants caused by temperature variations, differences in individual driving behavior, or contamination to the lubricant caused by seal leaks or other factors. Such premature degradation could occur prior to the end of the inspection interval, causing damage as previously discussed.

DE 19,644,029 A1 discloses a process for determining the functional suitability of a lubricant that lubricates slip-controlled clutches using a test vessel. The process tests different lubricants for their suitability for use in slip-controlled clutches. The process does not, however, determine the current state of a lubricant that is already being used to lubricate two cooperating frictional coupling elements.

Accordingly, there exists a need for a method of determining the current state of lubricant which is lubricating at least one pair of frictional coupling elements that transmit a torque when engaged.

SUMMARY OF THE INVENTION

It is an object of the invention to provide a method for determining the current state of a lubricant that lubricates at least one pair of frictional coupling elements arranged to cooperate and transmit a torque when engaged.

It is another object of the invention to prevent damage to frictional coupling elements and/or components connected to the frictional coupling elements resulting from inadequate lubrication of the frictional coupling elements.

The invention provides a method for determining the current state of a lubricant that lubricates at least one pair of frictional coupling elements which transmit a torque when engaged. The current slip characteristics of the coupling elements are determined and compared to reference slip characteristics which correspond to specific quality states of the lubricant. The current state of the lubricant is thereby determined.

Preferably, the reference slip characteristics are known for selected operating conditions. These selected operating conditions may include torque transmission, temperature and force exerted between the frictional coupling elements.

In a preferred embodiment, if an improper quality state of the lubricant is detected, a vehicle operator is signaled.

In another preferred embodiment of the present invention, the current slip characteristics are determined from the results of measuring the rotational speed of each coupling element.

In a further preferred embodiment, the comparing of current slip characteristics to the reference slip characteristics is performed by a processor such as a digital processor. In a highly preferred embodiment, the reference slip characteristics are stored in a memory associated with the processor.

In a highly preferred embodiment, determining the current state of the lubricant includes generating a signal when the value of the current slip characteristics differs from a reference slip characteristic value by a predetermined amount.

In this manner, a method of determining the current state of a lubricant lubricating two frictional coupling elements is provided and an operator may be signaled when the lubricant becomes degraded so the lubricant may be replaced before damage occurs.

Additional features and advantages of the invention appear in the following description of preferred embodiments of the invention, reference being made to the accompanying drawing which is incorporated and constitutes a part of this disclosure.

DESCRIPTION OF THE PRFERRED EMBODIEMENTS

Figure 1:
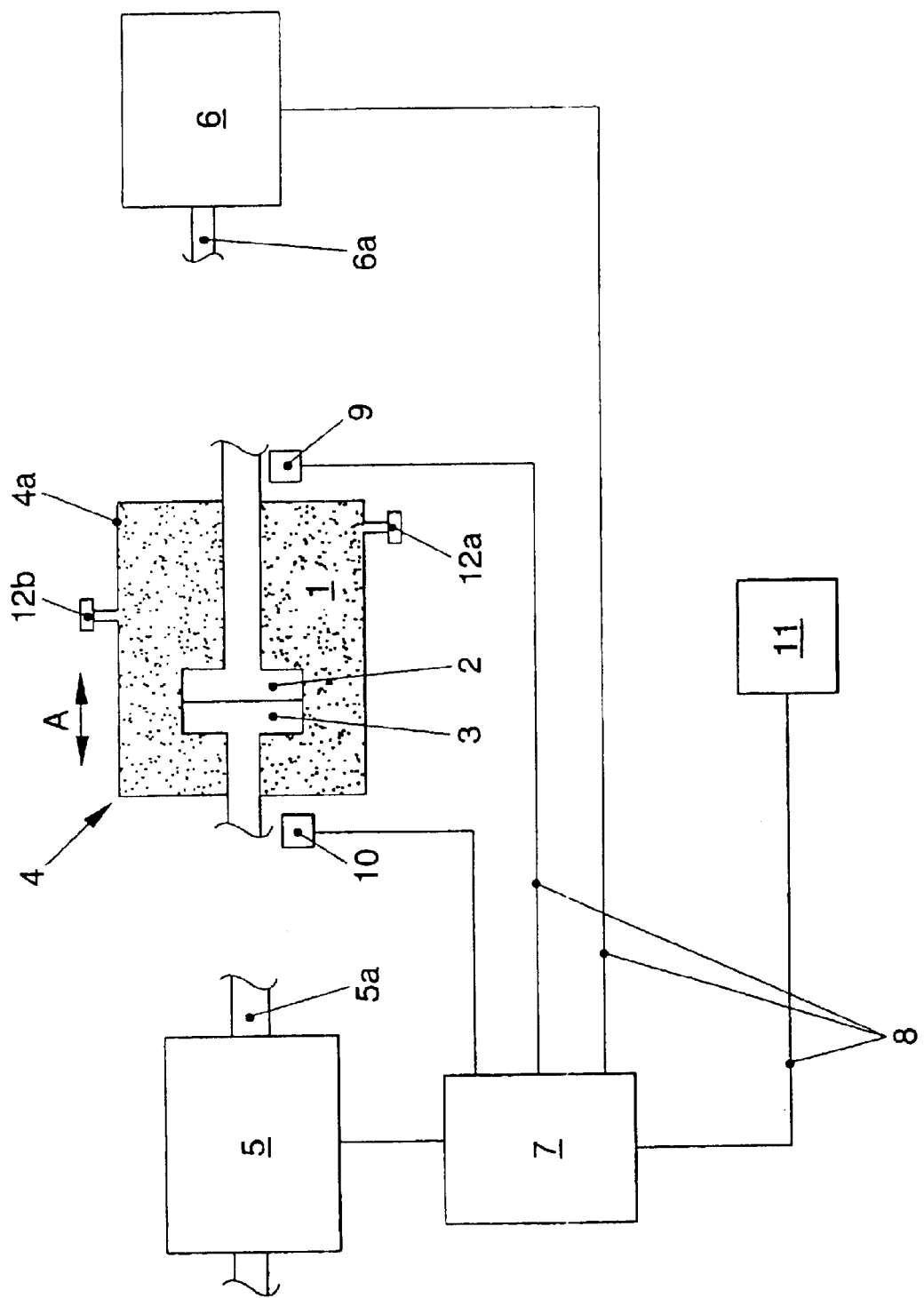
FIG. 1 is a simplified schematic representation of components for implementing the process according to the invention

In the simplified schematic representation of the components for implementing the process according to the invention represented in FIG. 1, reference is made to an automotive application of the present invention; however it will be apparent that the approach has general applicability to any system where at least two frictional coupling elements for transmitting a torque are lubricated, such as in machine transmissions or in a transmission clutch located outside of a transmission.

Referring to FIG. 1, a first frictional coupling element 2 and a second frictional coupling element 3 are arranged in a clutch housing 4a such that they can rotate and be lubricated by lubricant 1. In the automotive application of FIG. 1, the elements are implemented as part of a transmission clutch 4. The temperature of lubricant 1 may be detected by a temperature sensor not shown. The lubricant 1 may be drained out through orifice 12a or may be added through orifice 12b.

Transmission clutch 4 is located between a transmission 5 and engine 6, and thus transmits the torque from engine output shaft 6a to the transmission input shaft 5a when frictional coupling elements 2 and 3 cooperate through frictional engagement. Frictional coupling elements 2 and 3 may be brought into or out of engagement with one another as shown by arrow A. The engagement or disengagement of coupling elements 2 and 3 may be effected by an actuating device that is not shown in FIG. 1.

The control unit 7, which may be a general purpose digital processor, is connected to the transmission 5, the engine 6, a display device 11 and speed sensors 9 and 10 via control lines 8. Speed sensors 9 and 10 are capable of measuring the rotational speed of frictional coupling elements 2 and 3 respectively. Display device 11 can be activated to display an alert to a vehicle operator when lubricant 1 is no longer at the desired state, i.e. has become degraded.

The operation of control unit 7 is now described in detail. In a preferred embodiment of the present invention, reference slip characteristic values of frictional coupling elements 2 and 3 corresponding to operating points with specific parameters such as temperature, force between elements 2 and 3 and/or torque transmission values are measured at a time when lubricant 1 is known to be properly functioning, i.e. not yet overly aged or degraded. These reference values are stored in a memory associated with control unit 7. Preferably, the reference values are determined by comparing the rotational speed of element 2 as reported by speed sensor 9 with the rotational speed of element 3 as reported by speed sensor 10 at the operating point under investigation.

During vehicle operation, speed sensors 9 and 10 continuously report the rotational speeds of frictional coupling elements 2 and 3 to control unit 7. Additionally, other sensors not shown report other operating parameters such as temperature, torque transmitted and force exerted between coupling elements 2 and 3 to control unit 7. Control unit 7 then determines from the rotational speeds of elements 2 and 3 their current slip characteristics. From the operating parameter information, control unit 7 determines which of the reference slip characteristic values stored in its memory to compare to the determined current slip characteristics of elements 2 and 3. Having selected the appropriate reference characteristics for comparison, control unit 7 compares the current slip characteristics of the frictional coupling elements with reference slip characteristic values. If control unit 7 determines that the current slip characteristics of the coupling elements differs from the reference slip characteristics by a certain amount, it will generate a signal to display device 11, which in turn notifies the vehicle operator that the lubricant 1 has degraded and should be replaced.

In another embodiment of the present invention where multiple pairs of frictional coupling elements are lubricated by the same lubricant and the slip behavior of those multiple pairs of frictional coupling elements is measured independently of each other and reported to control unit 7, then control unit 7 can determine in a manner similar to that described above not only the current state of lubricant 1, but also whether the friction lining of these frictional shifting element pairs themselves have been damaged.

While there have been described what are believed to be the preferred embodiments of the present invention, those skilled in the art will recognize that other and further changes and modifications may be made thereto without departing from the scope of the invention, and it is intended to claim all such changes and modifications.

I claim:

1. A method for determining the current state of a lubricant which lubricates at least one pair of frictional coupling elements arranged to cooperate and transmit a torque when engaged, said pair of frictional coupling elements having reference slip characteristics associated with specific quality states of said lubricant, comprising determining current slip characteristics of said pair of frictional coupling elements, comparing said current slip characteristics to said reference slip characteristics and determining the current state of said lubricant from the results of said comparing, wherein said determination of the current state of a lubricant is performed in a vehicle during use.

2. The method as specified in claim 1 wherein said reference slip characteristics are known for selected values of operating conditions and wherein said current slip characteristics are compared to reference characteristics corresponding to the current operating conditions.

3. The method as specified in claim 2 wherein said operating conditions include torque transmission.

4. The method as specified in claim 2 wherein said operating conditions include temperature.

5. The method as specified in claim 2 wherein said operating conditions include force between said frictional coupling elements.

6. The method as specified in claim 1 wherein an improper quality state of the lubricant is signaled to a vehicle operator.

7. The method as specified in claim 1 wherein said determining current slip characteristics of said pair of frictional coupling elements comprises measuring the rotational speed of each coupling element of said pair of frictional coupling elements and determining current slip characteristics from the results of said measuring.

8. The method as specified in claim 1 wherein said comparing current slip characteristics to said reference slip characteristics is performed in a processor.

9. The method as specified in claim 8 wherein said reference slip characteristics are stored in a memory associated with said processor.

10. The method as specified in claim 1 wherein said determining the current state of said lubricant comprises generating a signal when the value of said current slip characteristics differs from a reference slip characteristic value by a predetermined amount.

11. A method for determining the current state of a lubricant which lubricates at least one pair of frictional coupling elements arranged to cooperate and transmit a torque when engaged, said pair of frictional coupling elements having reference slip characteristics associated with specific quality states of said lubricant, comprising determining current slip characteristics of said pair of frictional coupling elements, comparing said current slip characteristics to said reference slip characteristics and determining the current state of said lubricant from the results of said comparing, wherein said determining current slip characteristics of said pair of frictional coupling elements comprises measuring the rotational speed of each coupling element of said pair of frictional coupling elements and determining current slip characteristics from the results of said measuring.

12. A system for determining the current state of a lubricant, comprising:

a vehicle with a clutch housing;

a first frictional coupling element and a second frictional coupling element arranged within said clutch housing such that said first frictional coupling element and said second frictional coupling element can rotate and be lubricated by a lubricant;

at least one speed sensor coupled to said first and second coupling elements and which is capable of measuring the rotational speed of said first and second coupling elements; and a control unit comprising means for comparing the difference of the rotational speed of said first and second coupling elements with a reference value.

13. The system of claim 12 further comprising a display device for displaying an alert to an operator of said vehicle.

* * * * *